United States Patent [19]

Chang et al.

[11] Patent Number: 5,385,149
[45] Date of Patent: Jan. 31, 1995

[54] MAXIMUM PULSE WAVE AMPLITUDE CALCULATING SYSTEM AND OPERATION METHOD FOR AN ELECTRONIC BLOOD PRESSURE MEASURING DEVICE

[75] Inventors: Kyung S. Chang, Suwon; Sang B. Nam, Euiwang, both of Rep. of Korea

[73] Assignee: Samsung Electronics Co., Ltd., Suwon, Rep. of Korea

[21] Appl. No.: 125,176

[22] Filed: Sep. 23, 1993

[30] Foreign Application Priority Data

Sep. 23, 1992 [KR] Rep. of Korea .................... 92-17333

[51] Int. Cl.$^6$ .............................................. A61B 5/00
[52] U.S. Cl. .................................. 128/680; 128/681; 128/687; 364/413.03
[58] Field of Search ........ 128/668, 672, 677, 680-683, 128/ 687

[56] References Cited

U.S. PATENT DOCUMENTS

| | | | |
|---|---|---|---|
| 4,484,584 | 11/1984 | Uemura | 128/680 |
| 4,796,184 | 1/1989 | Bahr et al. | 128/681 |
| 4,917,116 | 4/1990 | La Viola et al. | 128/681 |
| 5,140,991 | 8/1992 | Niwa | 128/687 |

*Primary Examiner*—Lee S. Cohen
*Assistant Examiner*—Robert Nasser
*Attorney, Agent, or Firm*—Burns, Doane, Swecker & Mathis

[57] ABSTRACT

This invention, which comprises a cuff, an exhaust portion, a pressure sensor, an A/D converter, a microcomputer, a display, and an operation portion, initially determines the maximum pulse wave amplitude by comparing the size of each pulse wave, and it then determines the maximum pulse wave amplitude by comparing the sizes of the values obtained by totalling each pulse wave amplitude along with its preceding and subsequent pulse wave amplitudes, and it finally determines the maximum pulse wave amplitude by evaluating whether the different value between each preceding and each subsequent pulse wave amplitudes which occur after the maximum pulse wave amplitude has a negative(−) sign, thereby eliminating erroneous calculations caused by oscillation noise interference.

6 Claims, 4 Drawing Sheets

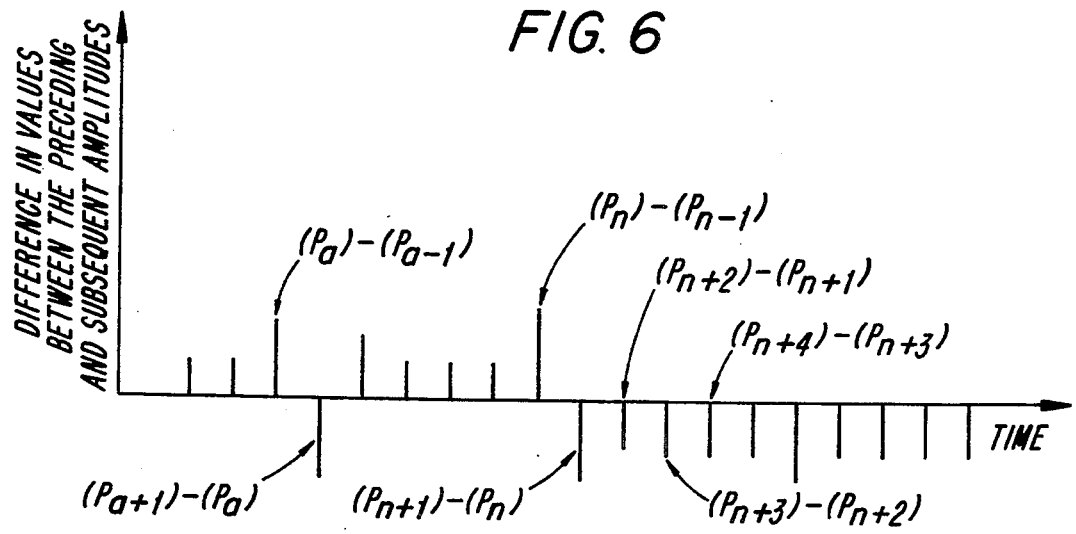

MAXIMUM PULSE WAVE AMPLITUDE CALCULATING SYSTEM AND OPERATION METHOD FOR AN ELECTRONIC BLOOD PRESSURE MEASURING DEVICE

BACKGROUND OF THE INVENTION

The present invention relates to electronic blood pressure measuring devices and more particularly, to maximum a pulse wave amplitude calculating system and operation method for electronic blood pressure measuring devices which can compensate for incorrect measurements of the maximum pulse wave amplitude—that is, the mean blood pressure—due to oscillation noise interference.

A prior art electronic blood pressure measuring device based upon the oscillation method includes a cuff which is wound around the upper arm of the person whose blood pressure is to be measured, a pressurization pump for pressurizing the cuff, an exhaust valve for exhausting the air within the cuff, a pressure sensor for detecting pulse waves and cuff pressure, an A/D converter for converting analog signals received by the pressure sensor into digital signals, and a microcomputer which receives pulse wave amplitudes and the cuff pressure from the converted digital signals, and calculates the maximum/minimum blood pressures by processing the information. In such a conventional electronic blood pressure measuring device, the method for calculating the maximum and minimum blood pressures from the cuff pressure and pulse waves is as follows.

Pulse waves are detected by the pressure sensor when the cuff pressure is gradually decreased after the blood flow in the patient's artery was momentarily stopped by pressurizing the cuff to a certain level.

The amplitudes of pulse waves, as shown in FIG. 3, form a graph curve which, with each amplitude, gradually increases until the maximum pulse wave amplitude Pn is recorded, and then diminishes over time.

In general, the maximum blood pressure pulse wave occurs at the cuff high pressure side corresponding to 50 percent of the maximum pulse wave amplitude, and the minimum blood pressure pulse wave occurs at the cuff low pressure side corresponding to 70 percent of the maximum pulse wave amplitude.

It is therefore important in the measurement of the patient's max./min. blood pressures to detect and identify the correct maximum pulse wave amplitude from among the numerous pulse wave components.

However, if an oscillation noise interference having a greater amplitude than the actual maximum pulse wave amplitude is present, the oscillation noise interference may be incorrectly identified as an actual maximum pulse wave amplitude. Because this incorrect maximum amplitude can cause an erroneous measurement of the max./min. blood pressures, all oscillation noises become important factors in potentially diminishing the accuracy of electronic blood pressure measuring devices.

The causes of such oscillation noise interference are as follows.

Even though the patient's heart generally generates regular pulse waves, sometimes irregular pulses may be included among them so that they create the possibility they will be incorrectly identified as maximum pulse wave amplitudes. Further, an oscillation noise interference may be caused by a momentary muscle jerk of the patient being evaluated.

Further, oscillation noise interference can be caused by the conscious or unconscious trembling of the patient being measured.

These kinds of oscillation noises can be identified as actual maximum pulse wave amplitudes when they are detected among the regular pulse waves sensed at the cuff.

FIG. 3 shows one typical cycle of pulse wave amplitudes sensed at the cuff when the cuff pressure for measuring the patient's blood pressures is decreased, where Pn represents the maximum pulse wave amplitude.

FIG. 4 illustrates a situation where a pulse wave amplitude Pa, made by any of the aforementioned oscillation noise interference, is larger than an actual maximum pulse wave amplitude Pn. Accordingly, the max./min. blood pressures are incorrectly measured because the microcomputer analyzing pulse wave components identifies the pulse wave amplitude by the oscillation noise Pa as the maximum pulse wave amplitude Pn.

SUMMARY OF THE INVENTION

It is an object of the present invention to provide a maximum pulse wave amplitude calculating system and operation method for electronic blood pressure measuring devices which can correctly measure a patient's blood pressures in spite of the presence of oscillation noise interference.

It is a further object of the present invention to'provide a maximum pulse wave amplitude calculating system and operation method for electronic blood pressure measuring devices which can provide an accurate measurement of the patient's blood pressures by the method of comparing the amplitude of each pulse wave, and the method of comparing the sizes of the values obtained by adding up each pulse wave amplitude plus the preceding and the subsequent pulse wave amplitudes of each wave amplitude, and the method of calculating whether the difference in values between the preceding and subsequent pulse wave amplitudes for each pulse wave which occurs after the maximum pulse wave amplitude is a negative(−) value, thereby eliminating pulse waves caused by oscillation noise interference.

The present invention comprises: a cuff wound around the body portion of a patient to limit the blood flow in the body portion; a pressurizing portion for pressurizing the air within the cuff to a certain predetermined level; a gradual exhaust portion for depressurizing the cuff by slowly exhausting the air from the cuff during the measurement of the blood pressure; a rapid exhaust portion for rapidly exhausting the air from the cuff after the blood pressure is measured; a pressure sensor for detecting cuff pressure and pulse waves necessary for determining the blood pressure during the reduction in the cuff pressure; an A/D converter for converting analog signals detected by the pressure sensor into digital signals in order for a microcomputer, which will be described hereinafter, to be able to evaluate the signals; a microcomputer for separately detecting the pulse waves and the cuff pressure, and calculating the maximum and minimum blood pressures by making use of the data; an operating portion for operating the electric power supply, the initiation of the measurement, and the setting of the cuff pressurizing value; and a display for displaying the measured results such as the max./min. blood pressures and the number of pulses, etc.

The process of measuring a patient's blood pressure by using the electronic blood pressure device of the present invention which is constructed as described above will now be explained below.

If the air within the cuff is gradually decreasing after being pressurized with the cuff wound around a patient's upper arm, the pressure sensor detects pulse waves occurring in the cuff according to the gradual decrease of the cuff pressure.

The detected analog signals are transmitted to the A/D converter and thereby converted into digital signals, and then they are transmitted to the microcomputer again.

In the microcomputer, a maximum pulse wave amplitude is initially determined from the received pulse wave amplitudes, which provides a base for calculating the max./min. blood pressures.

Normal pulse wave amplitudes excluding any oscillation noise interference during a set period are recorded so that a graph is computed wherein the amplitudes reach a maximum value through gradual increments, and then the amplitudes gradually decrease.

Therefore, the difference in values between the preceding and the subsequent pulse wave amplitudes are identified as being positive(+) numbers until the pulse wave amplitude reaches the maximum amplitude, and thereafter the values are identified as being negative(−) numbers.

However, in the event that any oscillation noise interferes with the normal pulse waves, the wave amplitude sequence changes.

The present invention is able to detect the actual maximum pulse wave amplitude because it records pulse wave amplitudes in a graph form covering a certain time interval. That is, when the microcomputer determines the maximum pulse wave amplitude, it uses an initial method in which the size of each pulse wave amplitude is compared, as done in a prior art, and then it uses a second method in which the sizes of the values obtained by adding each pulse wave amplitude with its preceding and subsequent pulse wave amplitudes are compared, and it then uses a third method of comparing the changes of the numeric positive or negative values obtained by calculating the difference between the preceding and subsequent pulse wave amplitudes for each wave amplitude.

Therefore, even when a particular oscillation noise having a larger amplitude than the actual maximum wave amplitude is present in the pulse waves data, the oscillation noise interference data can be excluded by performing the calculations according to the present invention because the difference between the amplitude of the oscillation noise and the amplitude of the subsequent pulse wave is a positive(+) value, and on the other hand, the difference between the amplitude of the preceding pulse wave and the amplitude of the noise oscillation is a negative(−) value so that the oscillation boise interference can be distinguished.

BRIEF DESCRIPTION OF THE DRAWINGS

The preferred embodiment of the present invention will now be described by way of example with reference to the accompanying drawings in which:

FIG. 6 is a graph showing the difference in values between each preceding and subsequent pulse wave amplitudes in FIG. 5;

FIG. 7 is a graph showing that the maximum pulse wave amplitude caused by an oscillation noise occurred near the actual maximum pulse wave amplitude; and, FIG. 8 is a graph showing the difference in values between each preceding and subsequent pulse wave amplitudes in FIG. 7.

DESCRIPTION OF THE PREFERRED EMBODIMENT

Figure 1:
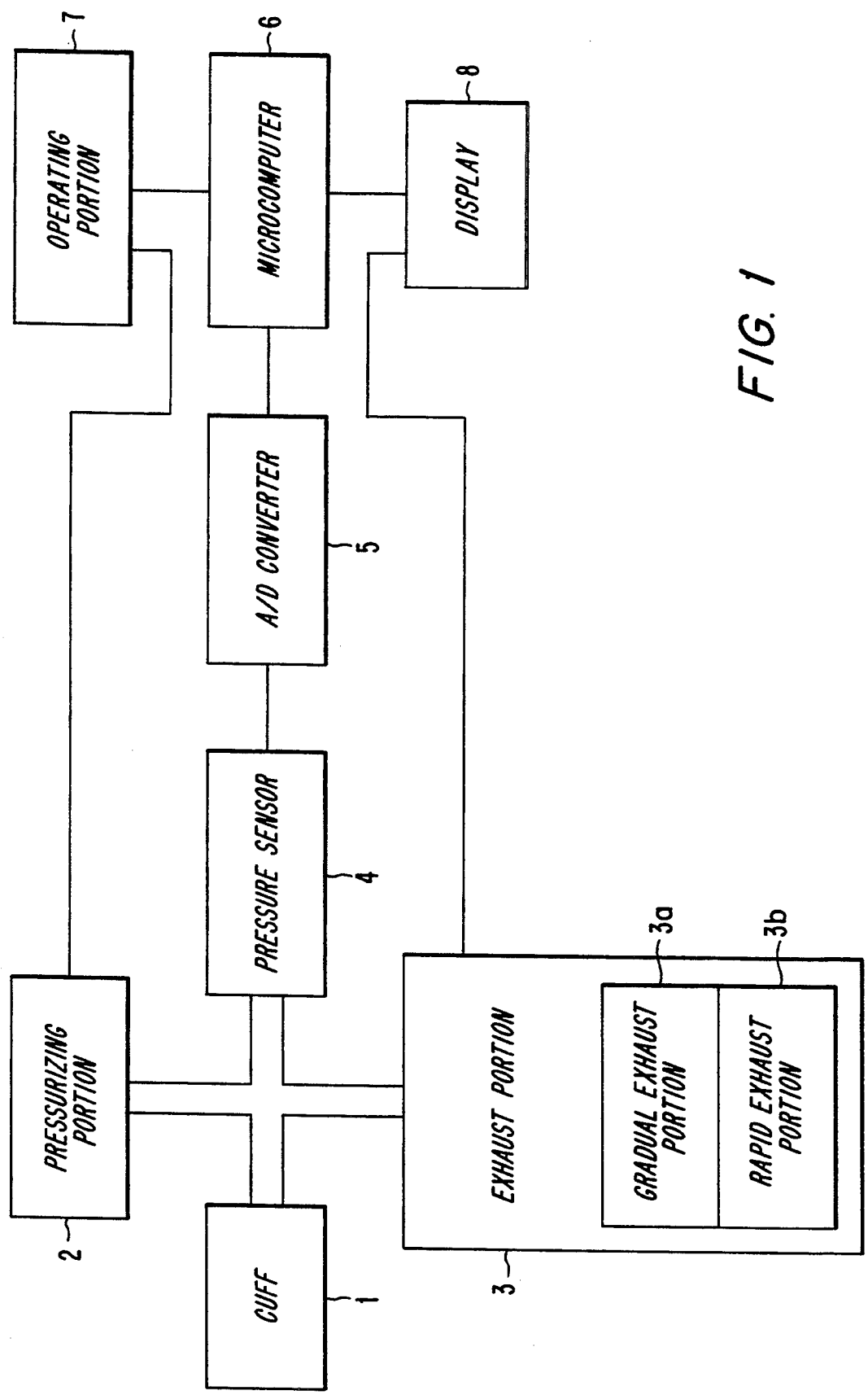
FIG. 1 is a block diagram of an electronic blood pressure measuring device according to the present invention.

The present invention will now be described in detail with reference to the drawings.

This invention comprises a cuff 1, a pressurizing portion 2, an exhaustion portion 3, a pressure sensor 4, an A/D converter 5, a microcomputer 6, an operating portion 7, and a display 8.

The cuff 1 is wound around a body portion (wrist, upper arm, finger, etc.) for measuring the patient's blood pressure, and is pressurized to a certain level by the pressurizing portion 2 in order to temporarily stop the blood flow.

The exhaust portion 3 includes a gradual exhaust portion 3a which gradually exhausts the air from within the cuff 1 during the measurement of the blood pressure, and a rapid exhaust portion 3b which rapidly exhausts the air from within the cuff 1 after the measurement of the blood pressure has been completed.

The pressure sensor 4 detects the pressures necessary for measuring the blood pressure and transmits them to the A/D converter 5. The A/D converter 5 converts analog signals received from the pressure sensor 4 into digital signals and transmits them to the microcomputer 6.

The microcomputer 6, which will be described in detail hereinafter, separately detects pulse waves and the cuff pressure from the digital signals received from the A/D converter 5, and determines the max./min. blood pressures and the pulse number by utilizing this data.

Further, since the microcomputer 6 is connected to the operation portion 7 and the display 8, it receives the initial blood pressure measurement data and the predetermined pressurization level, etc. from the operation portion 7, and has the display 8 indicate the max./min. blood pressures and the pulse number in accordance with the blood pressure measurement result.

Figure 2:
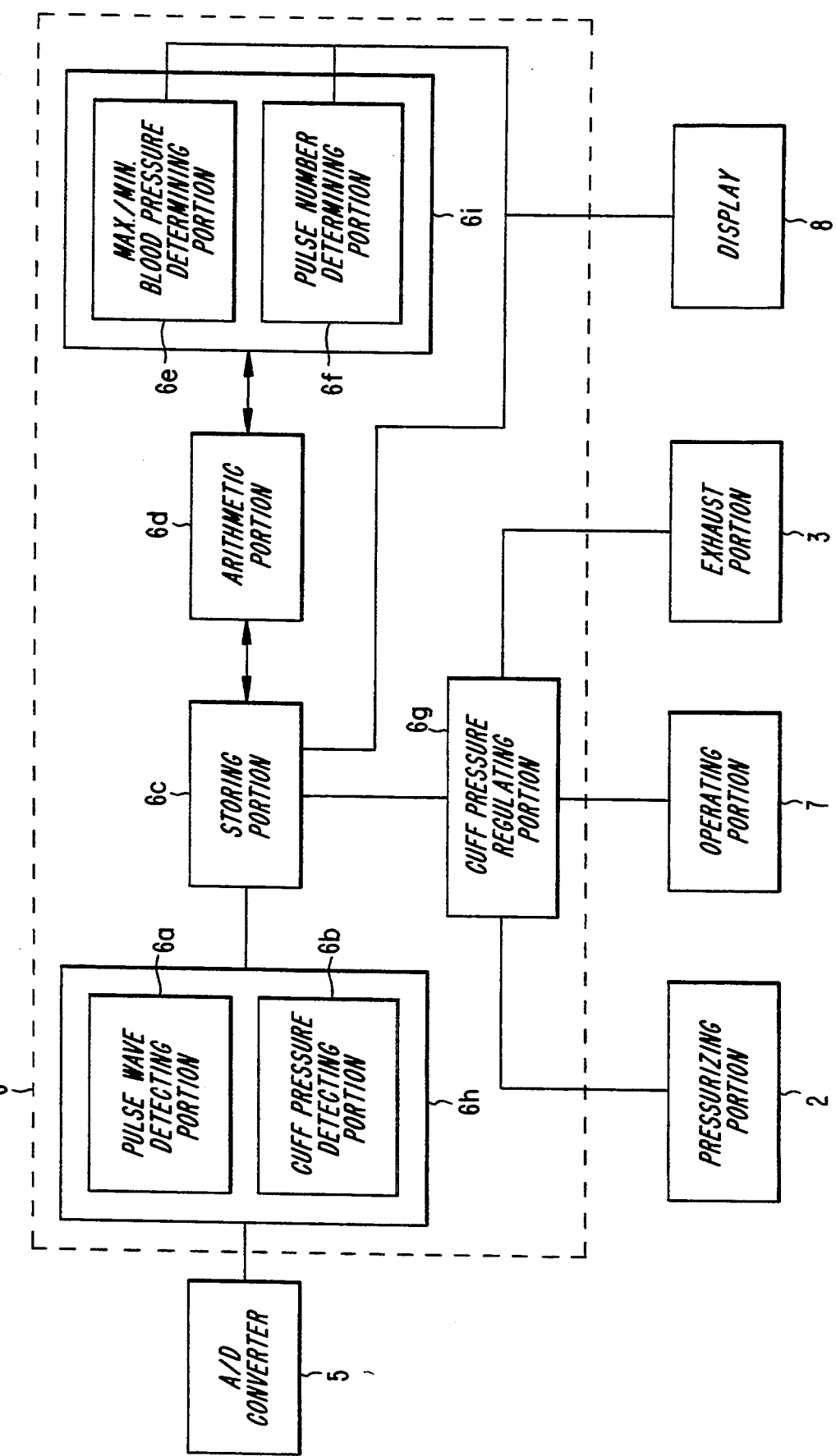
FIG. 2 is a block diagram showing in greater detail the construction of the microcomputer in FIG. 1.

As illustrated in FIG. 2, the microcomputer 6, which comprises a storing portion 6c, an arithmetic portion 6d, a cuff pressure regulating portion 6g, a detecting portion 6h, and a determining portion 6i, calculates the max./min. blood pressures and the pulse number based on the principle of the present invention.

Initially, the digital signals from the A/D converter 5 are transmitted to the detecting portion 6h which includes a pulse wave detecting portion 6a and a cuff pressure detecting portion 6b.

Accordingly, the detecting portion 6h detects individual pulse waves and the cuff pressure which is gradually decreased over time, and transmits the data to a storing portion 6c.

The storing portion 6c transmits the data on the pulse waves and the cuff pressure stored therein to the arithmetic portion 6d.

The arithmetic portion 6d, as described in detail hereinafter, compares the amplitudes of the above pulse waves in order to determine the maximum pulse wave amplitude, and it then calculates the maximum and minimum blood pressures by utilizing the determined maximum pulse wave amplitude. The calculated final data are transmitted to the determining portion 6i.

The determining portion 6i, which includes a max./min. blood pressure determining portion 6e and a pulse number determining portion 6f, determines the maximum and minimum blood pressures, and the pulse number based on the data received from the arithmetic portion 6d. Once the determination are completed, the values are displayed by the display 8, and the air within the cuff 1 is rapidly exhausted by the rapid exhaust portion 3b.

On the other hand, the arithmetic portion 6d calculates the maximum and minimum blood pressures by utilizing the following formulas based on the determined maximum pulse wave amplitude.

Maximum blood pressure $Pmax = A1 \times Pmean + B1$ ... (1)

Minimum blood pressure $Pmin = A2 \times Pmean + B2$ ... (2)

Mean blood pressure $Pmean = (2 \times Pmin + Pmax)/3$ ... (3)

Where, A1, B1 are constants necessary for calculating the maximum blood pressure, and A2, B2 are constants necessary for calculating the minimum blood pressure. The cuff pressure corresponding to the maximum pulse wave amplitude is the mean blood pressure.

Figure 3:
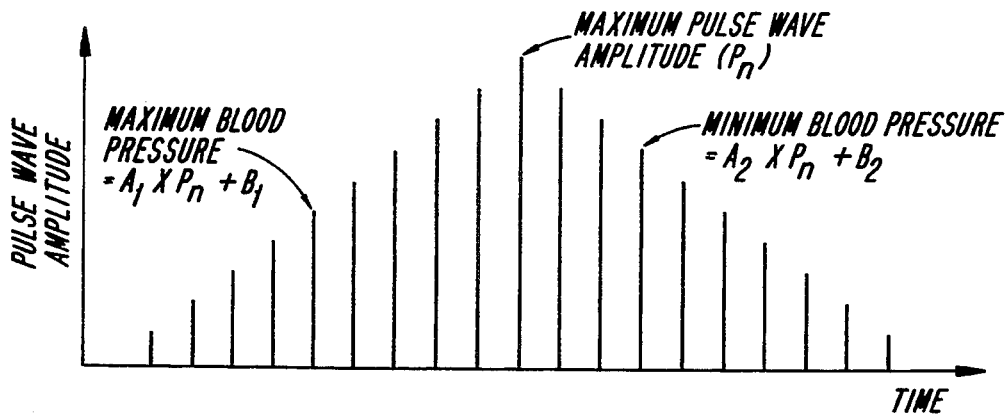
FIG. 3 is a graph representing pulse wave amplitudes in a given time sequence when the cuff pressure is gradually reduced.

The graph in FIG. 3, which illustrates the variations of the pulse wave amplitudes over time, shows that the value of a pulse wave amplitude reaches the maximum value Pn at the point where the values of the wave amplitudes cease gradually increasing over time, and thereafter begin gradually decreasing.

In this case, there is no difficulty in determining the correct maximum pulse wave amplitude.

But, when an oscillation noise is registered along with the pulse waves, a problem is that it is then difficult to correctly determine the mean blood pressure, that is, the maximum pulse wave amplitude Pn, because the oscillation noise interference is incorrectly registered as a maximum pulse wave amplitude so that the max/min blood pressures are incorrectly measured.

However, the present invention is able to eliminate an erroneous measurement of the blood pressure caused by oscillation noises.

Figure 5:
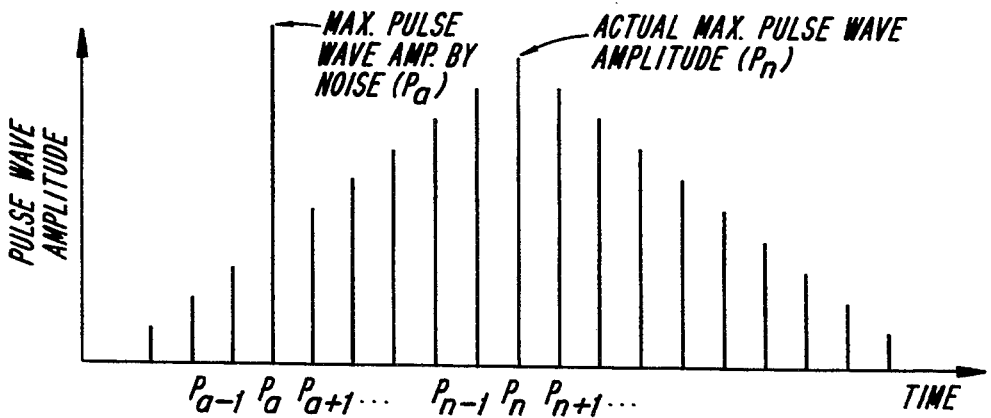
FIG. 5 is a graph showing an oscillation noise with a larger amplitude than the maximum pulse wave amplitude in FIG. 3.

When the noise amplitude Pa is larger than the actual pulse wave amplitude Pn as shown in FIG. 5, the electronic blood pressure measuring device of the present invention avoids any possible errors as follows.

A series of pulse wave data are sent from the pulse wave detecting portion 6a to the arithmetic portion 6d.

The arithmetic portion 6d initially compares the amplitude of each pulse wave to determine the maximum pulse wave amplitude Pn, and then it totals each pulse wave amplitude along with its preceding pulse wave amplitude and its subsequent pulse wave amplitude, and it then compares the waves' relative size to each other, thereby avoiding an erroneous calculation due to any oscillation noise interference.

For example, when the pulse wave amplitude caused by an oscillation noise Pa is larger than the actual pulse wave amplitude Pn, $Pa > Pn$ ... (4)

However, in connection with the neighboring pulse wave amplitude $(P_{a-1}) + (P_{a+1}) << (P_{n-1}) + (P_{n+1})$ ... (5)

Therefore, $(P_{a-1}) + (P_a) + (P_{a+1}) < (P_{n-1}) + (P_n) + (P_{n+1})$ ... (6)

Or, $\{(P_{a-1}) + (P_a) + (P_{a+1})\}/3 < \{(P_{n-1}) + (P_n) + (P_{n+1})\}/3$ ... (7)

Accordingly, even though the pulse wave amplitude caused by the noise Pa is larger than the actual pulse wave amplitude Pn, a maximum pulse wave amplitude is determined as Pn due to the relationship of the above inequalities (4), (5), and (6).

But, when the pulse wave amplitude caused by noise Pa occurs near the actual pulse wave amplitude Pn, a maximum pulse wave amplitude can not be correctly determined by relying only on the above method.

Figure 4:
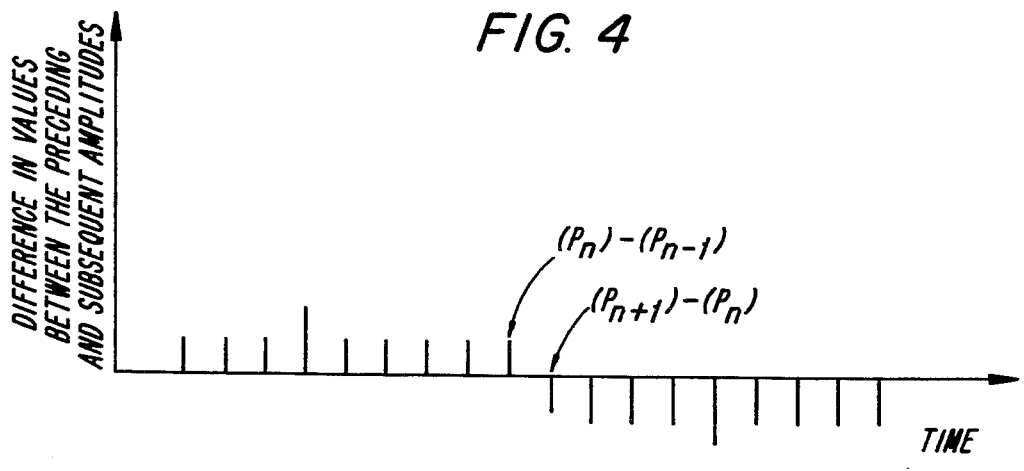
FIG. 4 is a graph showing the difference in values between each preceding and subsequent pulse wave amplitudes in FIG. 3.

In order to compensate for this imperfection, the electronic blood pressure measuring device of the present invention uses another method for evaluating the changes in the value signs which can be obtained by calculating the difference between the preceding pulse wave amplitude and the subsequent pulse wave amplitude for each pulse amplitude. That is, as shown in FIG. 4, when all oscillation noise interference is excluded, based on the actual maximum pulse wave amplitudes, the sign for the difference values between each preceding and subsequent pulse wave amplitude which occurs before the actual maximum pulse wave amplitude has a positive (+) sign, and the difference values between each preceding and subsequent pulse wave amplitude which occurs after the actual maximum pulse wave amplitude has a negative (−) sign.

But, as shown in FIG. 7, when the pulse wave amplitude caused by noise Pa occurs in the vicinity of the actual pulse wave amplitude Pn, the value obtained by subtracting the pulse wave amplitude caused by noise Pa from the subsequent pulse wave amplitude $(P_{a+1})$, that is, the value of $(P_{a+1}) - (P_a)$ has a negative(−) sign, and the value obtained by the calculation of the subsequent pulse wave amplitudes, that is, the value of $(P_{a+2}) - (P_{a+1})$ has i.e., $(P_a) - (P_{a-1})$ a positive(+) sign, and thereafter the values represent normal changes in the signs as in the pulse waves from which pulse wave noise interference has been excluded (FIG. 8). That is, the present invention is able to exclude any oscillation noises from the calculations by evaluating changes in the signs obtained by successively performing the arithmetic calculation of $(P_a) - (P_{a-1})$, $(P_{a+1}) - (P_a)$ ... $(P_n) - (P_{n-1})$, $(P_{n+1}) - (P_n)$, $(P_{n+2}) - (P_{n+1})$ ... FIG. 6 illustrates this method on the amplitudes shown in FIG. 5.

As a result, the present invention initially determines the maximum pulse wave amplitude by comparing the amplitude of each pulse wave, and then determines the maximum pulse wave amplitude by utilizing the aforementioned inequalities (4), (5), and (6), and finally it determines the maximum pulse wave amplitude by evaluating whether the difference in values between each preceding and each subsequent pulse wave amplitude which occurs after the maximum pulse wave amplitude has a negative(−) sign.

Because the electronic blood pressure measuring device of the present invention determines the actual maximum pulse wave amplitude by utilizing the aforementioned methods, it is able to eliminate erroneous calculations due to oscillation noise interference, thereby measuring the patient's correct max./min. blood pressures.

What is claimed is:

1. A maximum pulse wave amplitude calculating system for an electronic blood pressure measuring device comprising:
   a cuff;
   pressurizing means for pressurizing air within the cuff to a certain predetermined level;
   exhaust means for exhausting the air from the cuff;
   pressure sensor means for detecting pressures necessary for determining a patient's blood pressure;
   A/D converter means for converting analog signals detected by said pressure sensor means into digital signals;
   microcomputer means for separately detecting pulse wave amplitudes and cuff pressure, and calculating a maximum and a minimum blood pressure by utilizing said detected signals;
   operating means for operating an electric power supply, initiating blood pressure measurement, and setting a cuff pressure level; and
   display means for displaying the calculated pressures,
   wherein said microcomputer means includes arithmetic means which determines a maximum pulse wave amplitude by comparing sizes of values obtained by totalling each pulse wave amplitude with its preceding and subsequent pulse wave amplitudes, and determines whether said maximum pulse wave amplitude is an actual maximum pulse wave amplitude by evaluating, for each pulse wave amplitude which occurs after said maximum pulse wave amplitude, whether each value obtained by subtracting each subsequent pulse wave amplitude from each preceding pulse wave amplitude is a negative value.

2. A maximum pulse wave amplitude calculating system for an electronic blood pressure measuring device according to claim 1, wherein said display means displays the maximum and minimum blood pressures and a pulse number.

3. A method for determining a maximum pulse wave amplitude, comprising the steps of:
   (a) graphing amplitudes of pulse work signals detected by a pulse wave detector over a specific time period,
   (b) initially comparing the amplitude of each pulse wave signal to determine a maximum pulse wave amplitude,
   (c) determining whether the maximum pulse wave amplitude is an actual maximum pulse wave amplitude by comparing sizes of values obtained by calculating a sum of current, preceding and subsequent pulse wave amplitudes for each pulse wave amplitude,
   (d) further determining whether the maximum pulse wave amplitude is an actual maximum pulse wave amplitude by evaluating whether each value obtained by subtracting each current pulse wave amplitude from its preceding pulse wave amplitude which occurs subsequent to said determined maximum pulse wave amplitude is a negative value.

4. A method for determining the maximum pulse wave amplitude according to claim 2, wherein said step of determining comprises the step of determining that the maximum pulse wave amplitude not the actual pulse wave amplitude when the following relationships are true:

$(P_{1-1})+(P_{1+1}) << (P_{-1})+(P_{n+1})$, and $(P_{a-1})+(P_a)+(P_{a+1}) < P_{n-1}+(P_n)+(P_{n+1})$, or $\{(P_{n-1})+(P_a)+(P_{a+1})\}/3 < \{(P_{n-1})+(P_n)+(P_{n+1})\}/3$ wherein $P_n$ represents the actual pulse wave amplitude and $P_n$ is represents oscillation noise.

5. A method for determining the maximum pulse wave amplitude according to claim 4, wherein said step of further determining comprises the step of continuously performing the arithmetic calculation of . . . $(P_a)-(P_{a-1})$, $(P_{a+1})-(P_a)$, . . . $(P_n)-(P_{n-1})$, $(P_{n+1})-(P_n)$, $(P_{n+2})-(P_{n+1})$ . . . , to determine whether the maximum pulse wave amplitude is the actual maximum pulse wave amplitude by evaluating signs for the difference values between each preceding and subsequent pulse wave amplitudes.

6. A method for determining a maximum pulse wave amplitude for determining a maximum blood pressure using an electronic blood pressure measuring device, comprising the steps of:
   (a) storing amplitudes of pulse wave signals detected by a pulse wave detector over a specific time period,
   (b) initially comparing the amplitude of each pulse wave signal,
   (c) secondly determining a maximum pulse wave amplitude by comparing a size of the values obtained by calculating a sum of current, preceding and subsequent pulse wave amplitudes for each pulse wave amplitude,
   (d) finally determining whether the maximum pulse wave amplitude is an actual maximum pulse wave amplitude by evaluating whether each value obtained by subtracting each current pulse wave amplitude from its preceding pulse wave amplitude which occurs subsequent to said determined maximum pulse wave amplitude is a negative value, and
   (e) calculating said maximum and a minimum blood pressure values by using the determined actual maximum pulse wave amplitude.

* * * * *